United States Patent [19]
Colvin

[11] Patent Number: 5,491,092
[45] Date of Patent: *Feb. 13, 1996

[54] STERILIZER TEST METHOD AND APPARATUS

[76] Inventor: Richard R. Colvin, Orchard Hill Rd., Katonah, N.Y. 10536

[*] Notice: The term of this patent shall not extend beyond the expiration date of Pat. No. 5,422,276.

[21] Appl. No.: 263,801

[22] Filed: Jun. 22, 1994

Related U.S. Application Data

[63] Continuation-in-part of Ser. No. 878,564, May 5, 1992, abandoned.

[51] Int. Cl.⁶ ............................ G01N 30/54; A61L 2/24
[52] U.S. Cl. .................... 436/1; 436/3; 422/26; 422/109; 422/116
[58] Field of Search .......................... 436/1–6, 3–7; 422/26, 298, 109–111, 116

[56] References Cited

U.S. PATENT DOCUMENTS

| | | | |
|---|---|---|---|
| 3,967,494 | 7/1976 | Joslyn | 73/29 |
| 3,982,893 | 9/1976 | Joslyn | 21/2 |
| 4,115,068 | 9/1978 | Joslyn | 422/56 |
| 4,372,916 | 2/1983 | Chamberlain et al. | 422/111 |
| 4,486,387 | 12/1984 | Augurt | 422/58 |
| 4,594,223 | 6/1986 | Dyke et al. | 422/56 |
| 5,066,464 | 11/1991 | Augurt | 422/58 |

OTHER PUBLICATIONS

Bowie, J. H. et al, The Bowie and dick Autoclave Tape Test, The Lancet, Mar. 16, 1963, pp. 586–587.
Joslyn, L. J. citing Darmody et al, (1964) Disinfection, Sterilization and Preservation, S. Block, Ed., 3rd ed. 1983, p. 23.
Mayworm, D., The Bowie–Dick type test . . . Are there alternative ways?, Journal HSPD, Mar./Apr. 1984, pp. 31–34.
Ryan, P., The Bowie–Dick type test . . . The discrepancies between theory and practice, Journal HSPD, Mar./Apr. 1984, pp. 20–24.

Primary Examiner—Lyle A. Alexander
Attorney, Agent, or Firm—St. Onge, Steward, Johnston & Reens

[57] ABSTRACT

The operation of a steam sterilizer is monitored by a test unit and a controller which together comprise a system which can be operated in two principal method schemes: (1) the testing for completeness of air removal from a sterilizer chamber, and (2) the testing for effective sterilization conditions. These methods each have two principal modes of operation: (a) the performance of a Bowie and Dick type test, as is usually done on a once-a-day basis; and (b) monitoring the sterilizer during load conditions. In a preferred embodiment a test unit including temperature and pressure sensors, a moisture sensor and a heat sink are positioned within the chamber of a steam sterilizer and transmit by radio the conditions therein to an external controller. The test unit can employ a replaceable cartridge to assure effective operation even after a large number of cycles of operation.

20 Claims, 8 Drawing Sheets

STERILIZER TEST METHOD AND APPARATUS

RELATED APPLICATION

The present application is a Continuation-in-part of application Ser No. 07/878,564, filed May 5, 1992 now abandoned in the names of Richard R. Colvin and Herbert Perten.

TECHNICAL FIELD

The invention relates to sterilizers and, in particular, to a method and apparatus for improving the assurance of effective operation of sterilizers, especially those of the prevacuum type.

Reusable medical and surgical supplies must be cleaned and sterilized before storage for reuse. While absolute sterility may not be possible and testing for it is virtually impossible, strict adherence to stringent procedures can testing for it is virtually impossible, strict adherence to stringent procedures can provide confidence that no viable organisms should survive. Items like dressings, gowns, drapes, and instruments must be stored ready for use, and it is essential that procedures assure that no unprocessed packages are designated sterile.

Steam sterilization is the preferred method for use on an ongoing basis in hospitals. Conventional hospital practice entails the use of heat-activated indicator strips on each package to identify packages which have been treated in the sterilizer. The strips change color when heated sufficiently by the steam. A changed color strip does not, however, assure that the contents of the package have been heated sufficiently. This is assured only by rigorous adherence to established procedures for operating the sterilizer and for assuring its effectiveness when operated properly.

The leakage of air, and to a lesser extent the quality of steam in terms of superheating or wetness, can prevent a steam sterilizer from achieving its objective even though the proper times and temperatures are indicated on the sterilizer instruments. Short cycle times are preferred, but can be effective only when saturated steam directly contacts the objects of sterilization to permit transfer of the latent heat of vaporization to the objects and any microbiological contamination. Superheated steam does not condense, giving up its latent heat, as readily as saturated steam. In this regard, superheated steam is similar to hot air which alone, can sterilize, but it takes much longer and has the further problem that it does not mix well with steam. As a practical matter, air is an insulator. Wet steam can also cause an insulating effect by wetting fabric and inhibiting penetration of steam.

The presence of air in a steam sterilizer has always been a problem to be avoided. The pressure in the sterilizer and the condensation of steam in the packages tends to concentrate the air deep within the packages—preventing direct steam contact with the objects. To better free the sterilizer of air, many modern steam sterilizers employ a preliminary evacuation step. It is essential that evacuation be effective and that air does not have a chance to inhibit sterilization. Unfortunately, leaks of air are not uncommon. One investigator (Joslyn, citing Darmody et al (1964) in *Disinfection, Sterilization and Preservation;* S. Block, Ed.; Third Edition, 1983, page 23,) reported that not one of ten prevacuum sterilizers tested was able to meet and maintain recommended conditions.

In 1963, a test was suggested by researchers J. H. Bowie and J. Dick to determine if a prevacuum sterilizer was operating effectively in terms of air removal. (See J. H. Bowie, J. C. Kelsey, G. R. Thompson; The Bowie and Dick Autoclave Tape Test; *The Lancet,* Mar. 16, 1963, pp 586–7) Their procedure employed preparing a test package containing at least about 25 Huckaback towels folded into eight thicknesses and stacked to a height of 10–11 inches, a sheet of unglazed paper bearing a cross of a specific heat-sensitive tape placed in the middle of the stack, and a suitable wrapping. A nonuniform color change on the tape after subjecting the package to a complete sterilization cycle, indicated that air was present and sterility could not be assured. A uniform color change (supported by a record showing a satisfactory time-temperature relationship in the chamber drain) indicated a satisfactory result and could be interpreted as showing rapid steam penetration, adequate air removal, and freedom from significant air leaks.

The Bowie and Dick test was, however, subject to wide variations in the manner in which it was per- formed, and its results were very subjective. Indeed, one survey revealed that no two central service departments from a total of 35 interviewed, performed the Bowie and Dick test in the same way. (P. Ryan, The Bowie-Dick type test . . . The discrepancies between theory and practice, *Journal HSPD,* March/April 1984, pp. 20–24.) Another survey indicated the accuracy of interpreting test scores was only 60–80% at the beginning of a study. (D. Mayworm, The Bowie-Dick type test . . . Are there alternative ways?, *Journal HSPD,* March/April 1984, pp. 31–34.) The reliability of steam sterilizers in the medical field remains an active area of concern and research.

Bowie and Dick type tests are typically run once a day and, if run and interpreted correctly, can determine only the condition of air leakage and can determine it only at that time. The sterilizer operations which are actually responsible for assuring the safety of patients are conducted under load conditions and cannot be monitored with accuracy with current technology. There is a present need for a more objective, less subjective, more accurate test for adequate air removal, as well as a test which can reliably, automatically monitor sterilization conditions.

BACKGROUND ART

Over the years, a number of devices and techniques have been proposed to provide a greater degree of assurance that a sterilizer is operating effectively to exclude air which could prevent direct contact of steam with the objects being sterilized. In some cases, these have been adopted by hospitals convinced that they needed more reliability.

Efforts to mechanically assure the complete removal of air from steam sterilizers have not been fully successful. Prior to the publication of the Bowie and Dick test in 1963, co-developer J. Dick had employed thermocouples in a simpler form of the test, one in a test package and another at the sterilizer drain. With most loads like the towel package, however, it is not possible to predict the location of the air bubble with the certainty required. The published version of the test replaced the thermocouple with a heat-sensitive tape to better indicate the extent of air incorporation, but still required monitoring drain temperatures. In U.S. Pat. No. 3,967,494, Joslyn disclosed a method and apparatus for detecting entrapped air in a steam sterilizer. The device is shown outside the steam chamber to enable quantitative measurement of the amount of air or other noncondensible gas at the chamber drain. The device is intended for use with a sterilizer of the type that employs steam to displace air. The device does not, however, eliminate the need for a Bowie and Dick test.

In U.S. Pat. No. 4,372,916, Chamberlain and Cook monitor the temperature of the exhausted steam at the drain and the pressure within the chamber, and compare these to the steam table values to determine if all the air has been evacuated. The positioning of sensors within the chamber, especially by retrofitting, can, however, create further problem areas for future concern.

In U.S. Pat. No. 4,115,068, Joslyn describes a small device for indicating air inside a sterilization chamber of the type used with steam or ethylene oxide. The device includes an upright tube holding an indicator strip and a heat sink. Air is said to pass into the tube where it interferes with the steam contacting the indicator strip. Dyke and Oshlag comment on this arrangement in U.S. Pat. No. 4,594,223, indicating that steam, which is less dense than air, is required to work against the weight of any accumulated air. To correct this, they describe a device having a depending glass chamber which permits air to settle to the bottom along with water from condensed steam. This device, like that of Joslyn, is simply a replacement for the Bowie and Dick test and requires interpretation of the test results—a source of frequent errors in the original Bowie and Dick test. This is true also of a related device disclosed by Augurt in U.S. Pat. No. 5,066,464, which has a strip of heat-sensitive material in a horizontally-disposed chamber. Similarly, U.S. Pat. No. 4,486,387 to Augurt and U.S. Pat. No. 4,596,696 to Scoville, describe disposable test packages which have Bowie and Dick type test sheets which require interpretation.

There remains a need for a method and apparatus to more objectively, reliably, and precisely determine the effective operation of a steam sterilizer. There is especially a need for a test which provides a positive indication of problems or the absence of them and decreases the probability that either (1) the test performance or (2) interpretation of the results will be dependent upon the skills of a particular operator—both, areas of concern in Bowie and Dick testing.

DISCLOSURE OF INVENTION

It is an object of the invention to provide a test method and apparatus to determine the effective air removal from a steam sterilizer with less subjectivity, and therefor, greater accuracy than the Bowie and Dick test.

It is an object of the invention to provide an electronic test method and apparatus for determining the effectiveness of air removal from a steam sterilizer and thereby reduce common causes of error in Bowie and Dick type tests.

It is another object of the invention to provide a method and apparatus for monitoring the sterilization conditions within a steam sterilizer as desired for a Bowie and Dick test cycle or operation under load conditions.

It is another and more specific object of the invention to provide a method and apparatus for monitoring a steam sterilizer operation under load conditions for the presence of wet steam, superheated steam and air.

It is an additional object of the invention to provide a reliable test method and apparatus for monitoring the operation of prevacuum sterilizers which can determine the effective evacuation of air and the quality of the steam in terms of superheating and/or wetness.

It is yet another object of the invention to provide an apparatus and method for determining the effective air removal from the chamber of a steam sterilizer and/or steam quality therein by placing a portable test unit in the chamber and either recording the data sensed by the unit internally or transmitting it by radio to a receiver outside the chamber.

It is a further object of the invention to provide an early warning system for a steam sterilizer which can determine the effective air removal from a prevacuum sterilizer and/or steam quality therein by comparing real time readings to either or both of standard values and average values for recent test runs for both a Bowie and Dick test cycle mode and for operation under load conditions.

It is yet another specific object of the invention to provide a method and apparatus for determining the effective air removal from the chamber of a steam sterilizer by placing a portable test unit in the chamber and either recording the data of the unit internally or transmitting it to outside the chamber by radio.

These and other objects are accomplished by the present invention which provides methods and apparatus for determining the effectiveness of air removal from a steam sterilizer and for monitoring the sterilization conditions therein. The apparatus provides a test device, a controller and a system which utilizes one or both. The methods achieve the objects of the invention in its broad as well as specific aspects.

In one of its preferred forms, the test device comprises: a wall member defining an elongated test cavity having an opening at one end to permit entrance of ambient gases;

a temperature sensor capable of generating a signal ($T_1$) indicative of the temperature at its location at an end of the test cavity opposite from said opening; and a heat sink located in said test cavity between said opening and said temperature sensor, said heat sink comprising a material of a density, porosity and thermal conductivity effective to condense a sufficient amount of steam to cause air, if present, to collect at the end of the test device where the temperature sensor is located. In another of its preferred forms the test device will comprise: means for sensing the temperature at a location within a sterilization chamber and generating a signal ($T_1$) indicative thereof; and radio transmission means for transmitting signal $T_1$ to a location outside of the sterilization chamber. It is preferred to provide means for recording the time at which a temperature or other value is taken. In yet another, storage means are provided for storing signal $T_1$ within said chamber.

The controller in one of its preferred forms comprises: means for receiving a signal ($T_1$) indicative of the temperature at a predetermined location within the chamber of a steam sterilizer; means for generating a signal ($T_r$) indicative of a reference temperature (and preferably the time at which it was taken), which can be either a preselected reference temperature such as the desired sterilization temperature or a calculated temperature such as the average of selected temperatures reported in the latest of a predetermined number of cycles of operation in either two modes (namely, (1) Bowie and Dick test or (2) operation under load); means for comparing signal $T_1$ to signal $T_r$; and means for generating a signal indicative of either a pass or fail condition based on the results of the comparison. The means for receiving the signal $T_1$ can comprise a radio receiver or connector means to electrically couple the controller to the test device.

The system in one of its embodiments comprises: a test device capable of sensing the temperature (and preferably the time at which it was taken) at its location and generating a signal ($T_1$) indicative thereof said test device comprising a temperature sensor and means, having an elongated cavity with an opening at one end of the cavity to permit the entrance of steam, a temperature sensor within the cavity displaced from the opening, and a heat sink capable of condensing steam disposed within the cavity between the opening and the temperature sensor, for concentrating air to the location of said temperature sensor, said heat sink comprising a material of a density, porosity and thermal conductivity effective to condense a sufficient amount of steam to cause air, if present, to collect at the end of the test device where the temperature sensor is located;

means for generating a signal ($T_r$) indicative of a reference temperature (and preferably the time at which it was taken), which can be either a preselected reference temperature such as the desired sterilization temperature or a calculated temperature such as the average of the last temperature reported in the latest 10 cycles of operation;

means for comparing signal $T_1$ to signal $T_r$; and means for generating a signal indicative of either a pass or fail condition based on the results of the comparison.

The method of the invention in one of its forms comprises: placing a test device capable of concentrating air to the location of a temperature sensor and of sensing a temperature by means of said temperature sensor within the chamber of a sterilizer and generating a signal ($T_1$) indicative of the sensed temperature (and preferably the time at which it was taken), said test device including an elongated cavity having an opening at one end of the cavity to permit the entrance of steam, a temperature sensor within the cavity displaced from the opening, and a heat sink capable of condensing steam disposed within the cavity between the opening and the temperature sensor to thereby concentrate any air present in the direct vicinity of the sensor, said heat sink comprising a material of a density, porosity and thermal conductivity effective to condense a sufficient amount of steam to cause air, if present, to collect at the end of the test device where the temperature sensor is located; generating a signal $T_1$; generating a signal ($T_r$) indicative of a reference temperature; comparing signal $T_1$ to signal $T_r$; and generating a signal indicative of either a pass or fail condition based on the results of the comparison.

BRIEF DESCRIPTION OF THE DRAWINGS

The invention will be better understood and its advantages will be more fully appreciated from the following detailed description, especially when read in light of the accompanying drawings, wherein.

DESCRIPTION OF PREFERRED EMBODIMENTS

The description which follows will focus on a preferred test unit and a preferred controller which together comprise a preferred system of the invention. This apparatus will be described in terms of the performance of the two principal method features of the invention: (1) the testing for completeness of air removal from a sterilizer chamber, and (2) the testing for effective sterilization conditions. These methods will be illustrated for the two principal modes of operation: (a) the performance of a Bowie and Dick type test, as is usually done on a once-a-day basis; and (b) monitoring the sterilizer during load conditions. The invention will be described in the specific context of prevacuum steam sterilizers, but is not strictly limited to sterilizers of this type.

Figure 1:
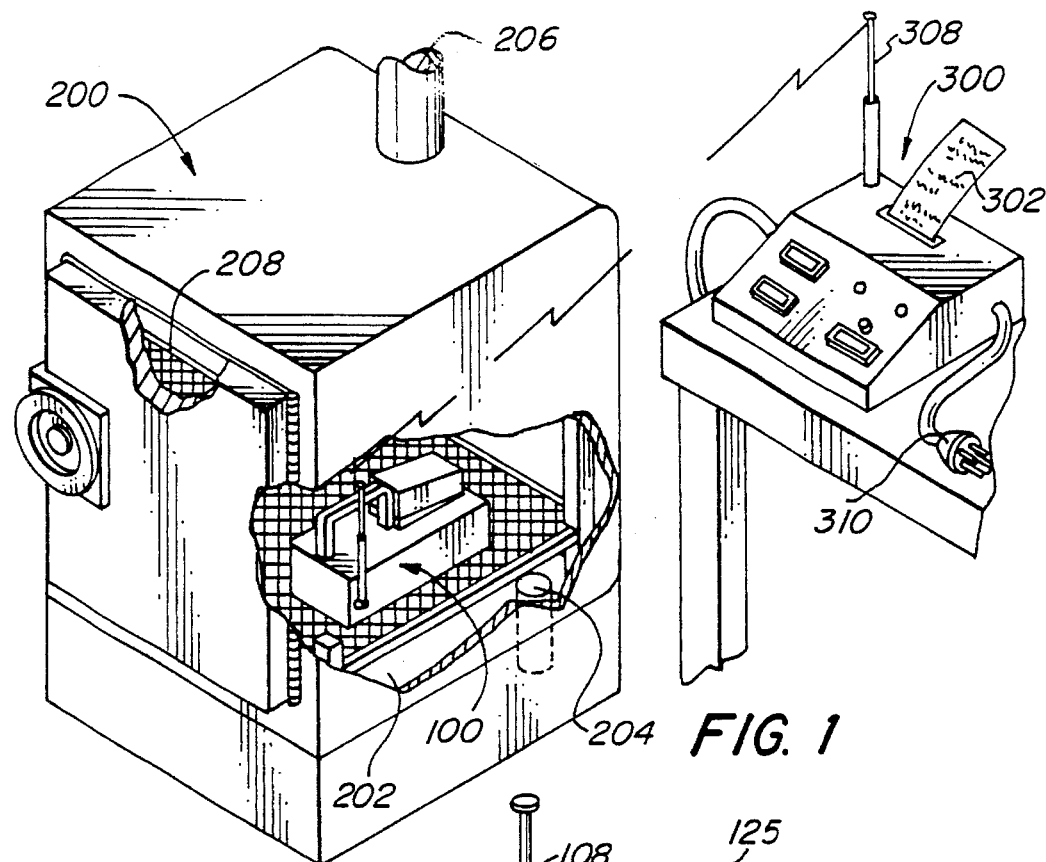
FIG. 1 is a perspective view of a preferred system of the invention including a test unit inside the chamber of a steam sterilizer, positioned for recording test data and transmitting by radio to an external controller unit.

FIG. 1 illustrates a preferred system of the invention which includes a test unit 100 inside the chamber 202 of a sterilizer 200. The test unit is shown positioned near drain 204, for obtaining data and transmitting via radio frequency to controller 300 which is shown outside of the chamber 202. The system can operate by obtaining temperature data alone or in combination with pressure and/or dispersed liquid moisture data. The data can be transmitted from the chamber by radio to provide real time monitoring, or it can be stored within the test unit 100 for later transmission to controller 300 such as through electrical connection, infra red data transmission, or other suitable means. Whatever means of transmission are selected, a permanent archiveable record 302 can be generated by display means such as a thermal printer or a chart recorder. This enables accurate records to be kept, whether the system is operated in a mode to perform a Bowie and Dick type test (Bowie and Dick mode) or in a mode to monitor the operation of the sterilizer under load conditions (load mode).

Figure 2:
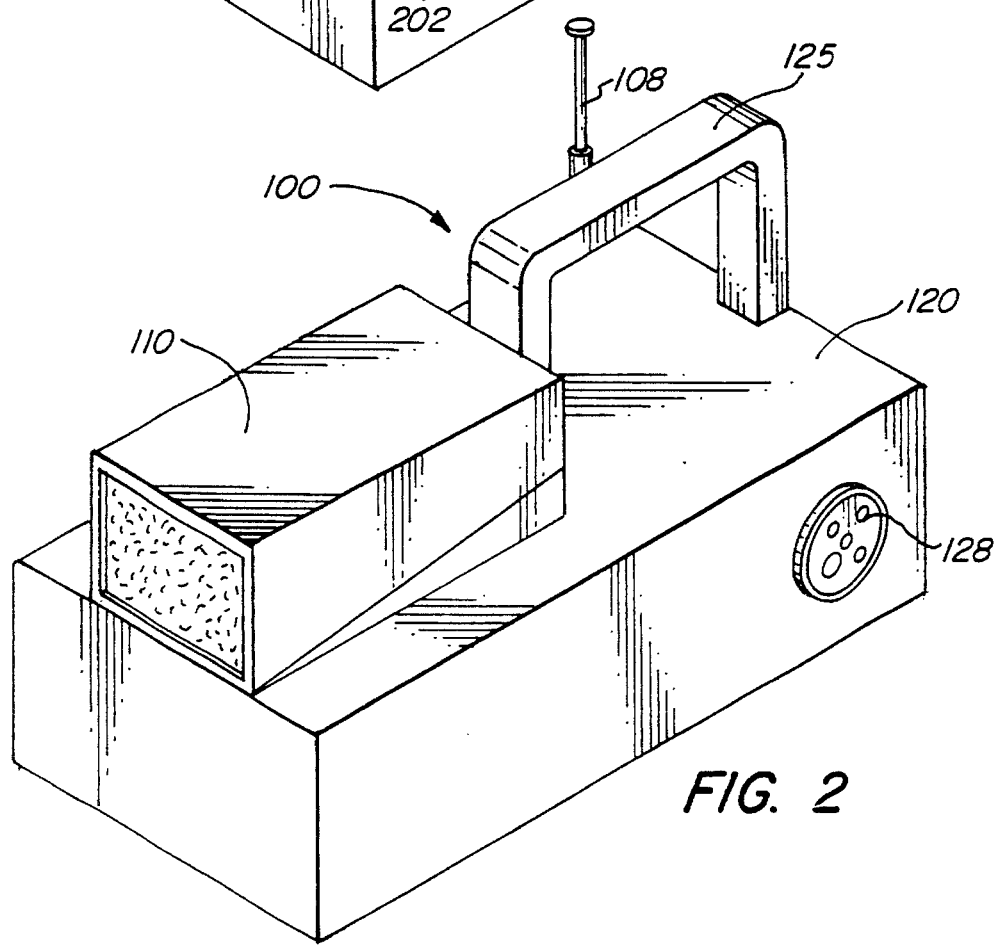
FIG. 2 is a perspective view of a preferred form of test unit of the invention.
Figure 5:
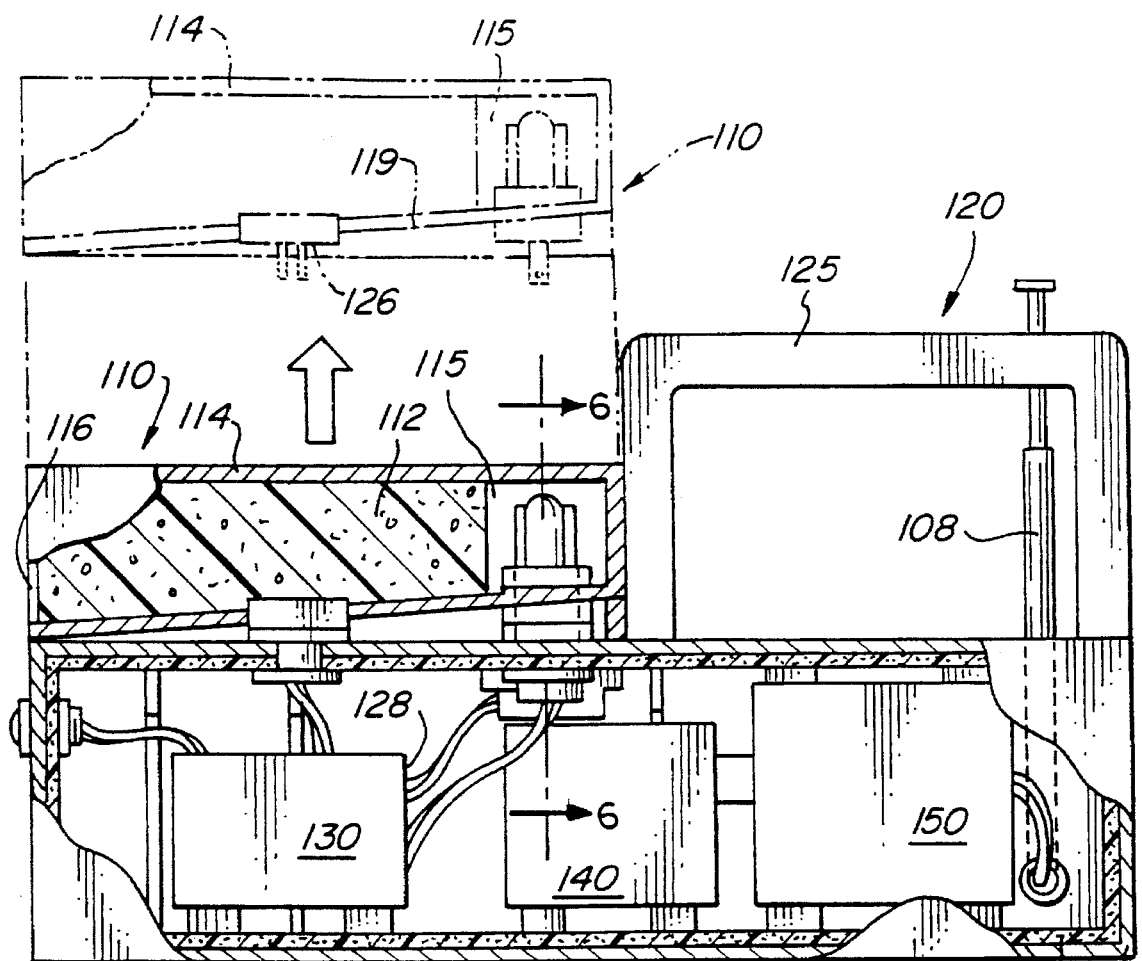
FIG. 5 is a side elevation view of the test unit shown in FIG. 2, partially cut away to illustrate major components.
Figure 6:
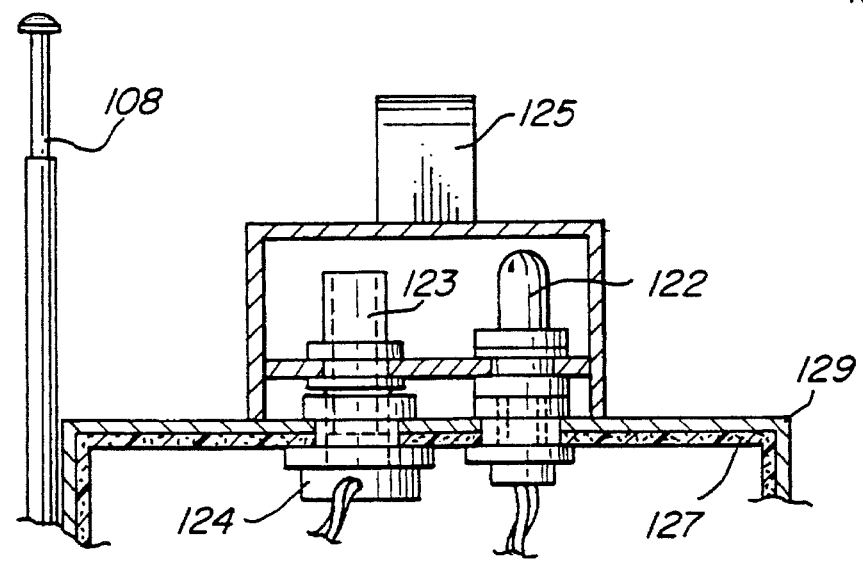
FIG. 6 is a cross-sectional view taken along line 6—6 in FIG. 5.

FIG. 2 shows a preferred form of test device of the invention in greater detail, as do the partially cut away view of FIG. 5 and the sectional view of FIG. 6. The test unit 100 is seen to be comprised of two principal components, illustrated as a replaceable test module 110 and a data collection and transmission unit 120. In the embodiment shown, data is transmitted via radio circuitry from transmission unit 120 via antenna 108 as will be described in greater detail below. Preferably, means are also provided to store the data within the unit 100 for later processing. It is also possible to provide a test unit such as 100 which is not equipped with radio transmission means.

Figure 7:
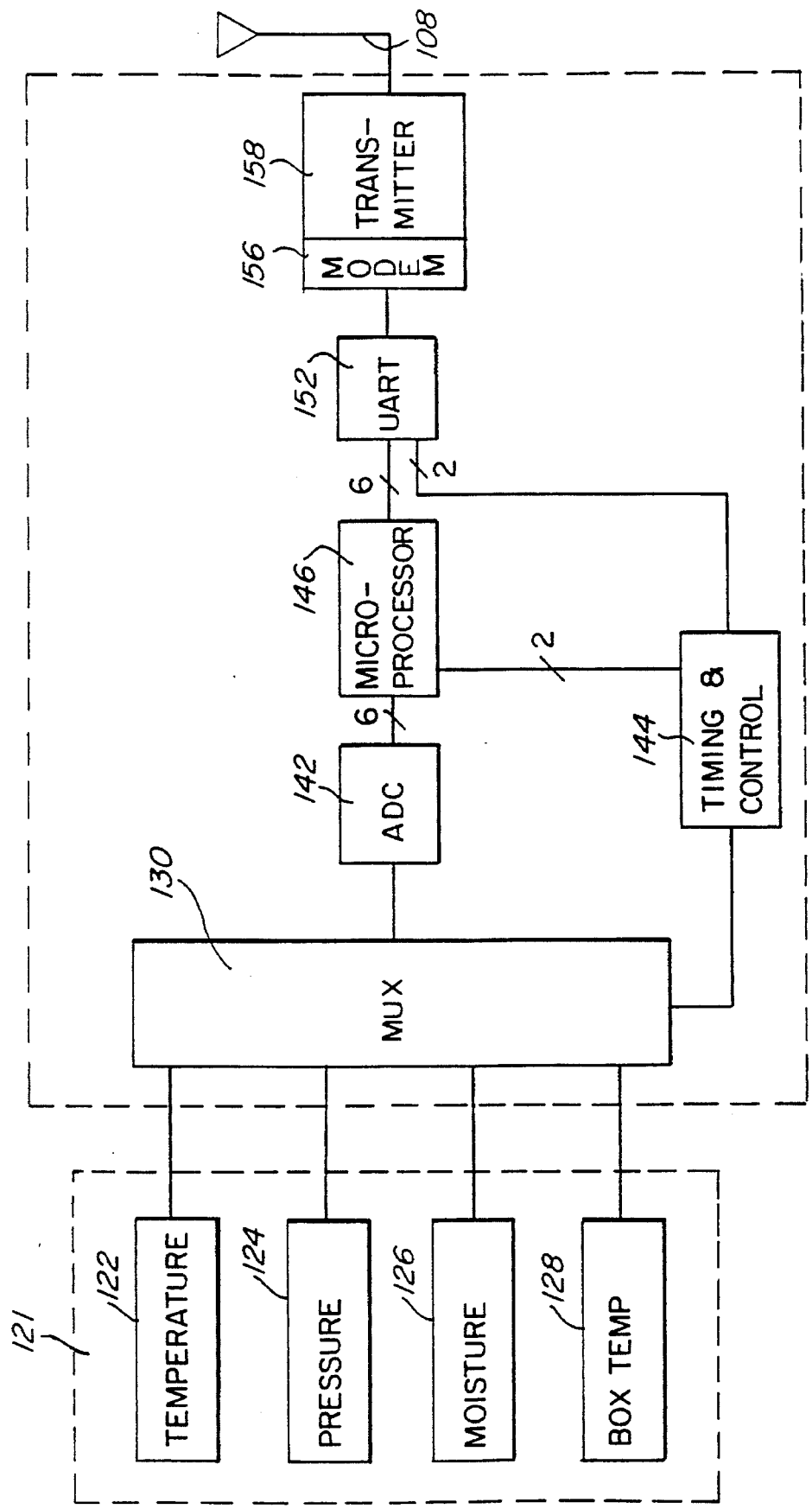
FIG. 7 is a block diagram of the circuitry for a test unit such as shown in FIG. 2.

FIG. 7 corresponds to FIG. 5 by showing the major components in block diagram form. Included are an array of sensors 121, namely temperature sensor 122, pressure sensor 124, moisture sensor 126, and box temperature sensor 128. Temperature sensor 122 is preferably a solid state temperature transducer, such as an Analog Devices (Maynard, Mass.) model AD 590 with a resolution of 0.5° F. and a measurement range of 257°–286° F. The pressure sensor 124 is preferably a pressure transducer as shown in FIGS. 5 and 6. The temperature sensor 122 and port 123 to the pressure sensor 124 are shown as component parts of replaceable test module 110. The moisture sensor 126 is desirably embedded within heat sink material 112 in the test module 110. The temperature sensor 128 will be embedded within or closely associated with the temperature-sensitive electronic components, such as multiplexer 130 within the transmission unit 120. The temperature sensor 128, can be similar to sensor 122 and is capable of generating a signal indicative of the temperature within the transmission unit 120 to warn of overheating.

The temperature sensor 122, senses the temperature within test cavity 115 located at a position in the sterilizer, usually near the drain 204, where it would be most sensitive to the presence of air. All of the test devices of the present invention have the capability of obtaining temperature data by sensing the temperature within a chamber 202 and generating a signal indicative of that temperature.

The pressure sensor 124 is optional, but preferred, and provides the ability to sense the pressure at the location of the sensed temperature and to generate a signal which corresponds to it. The pressure sensor 124 is preferably located within the transmission unit 120, but is open to the test module 110 through port 123 which can simply be a tube which fits into the transducer.

The moisture sensor 126, is also preferred, but optional, and adds the ability to sense the presence of liquid water dispersed in the steam. Most modern sterilizers include moisture traps near the steam inlet, e.g., at 206, to maintain wet steam at low levels, but it is an added advantage of the invention that assurance can be provided to reduce the chances that wet loads could result due to steam moisture contents greater than a target level, usually a maximum of 3%. Suitable for this purpose are moisture sensors such as those described by Smith in U.S. Pat. No. 4,909,070.

The replaceable test module 110 is designed to concentrate air to the specific location of the temperature sensor 122. It is shown to simply comprise a wall member 114 which defines an elongated test cavity 115 having an opening 116 to one end to permit entrance of ambient gases, a temperature sensor 122 as described, and a heat sink 112 in the cavity between the temperature sensor 122 and the opening 116. The heat sink can be of any suitable material which is capable of condensing steam and retaining the condensed steam therein. The heat sink material should be of a density, porosity and thermal conductivity to condense a sufficient amount of steam to cause air, if present, to collect at the end of the test chamber where the temperature sensor 122 is located. It is preferably absorbent enough to hold condensed water and, yet, dry rapidly. Gauzes or felts of cotton with or without metallic fibers should be effective as will standard central supply wrap or open-celled polymer foam.

Under conditions of use the test unit is placed within sterilizer 200 and is subjected to a vacuum before steam is applied. Steam, when introduced, will enter opening 116 and will progress into cavity 115 wherein it will begin to condense in heat sink 112. If any air is present in the steam due to a defective chamber seal, such as rubber seal 208 (or defective vacuum pump or piping), the air will remain uncondensed as the steam around it condenses. As this process continues, air, to the extent present, will concentrate at the rear of test cavity 115 and insulate the temperature sensor 122 from the heat of the steam.

If the steam is too wet, this could cause wet loads which are difficult to dry and are more easily recontaminated and may interfere with obtaining effective temperature readings. It is therefore desired to employ a moisture sensor 126.

The replaceable test module 110 is desirably in cartridge form which can simply be snapped into and out of position (see FIG. 5). It is recommended that these modules be replaced periodically, e.g. weekly or monthly, and whenever subjected to excessively wet steam. Good hospital practice would dictate eliminating the variability which could arise by using a wet test module or one which has been used for a period of time which would permit corrosion of the sensors or degradation of the heat sink material 112 by steam. When employed in the load mode to monitor the conditions during sterilization, the cartridges may be changed after each cycle to assure that a dry cartridge at room temperature is present at the start of each run. These cartridges may be reused several times. In one embodiment, it is desirable to provide means for preventing operation of the unit in the load mode unless the cartridge has been replaced.

Another feature of the cartridge is the provision of bottom wall 119 which slopes away from the sensors to prevent liquid water from collecting at that location. When placed on a level surface, liquid water flows toward opening 116.

Referring again to FIG. 5, the transmission unit 120 is shown to have a casing 129 with an internal layer of insulation 127 (shown here as foamed plastic) and an external handle 125 for ease of handling. Potting in a high-mass, low-thermal-conductivity material is also effective. The casing and insulation together should provide temperature protection for the sensitive internal components up to at least about 290° F., a vacuum of less than one-half inch of mercury and a pressure differential of at least 5 atmospheres. The transmitting antenna 108 is a length of ¼-wave wire located perpendicular to the base of casing 129 which acts as a ground plane.

Transmission of the data is effected by unit 150 shown in FIG. 5 which includes UART 152 (universal asynchronous receiver-transmitter), modem 156 and radio transmitter 158. Specifically, the UART can be an Intersil 6402 unit and the modem and transmitter can be combined as in an FM unit such as a Motorola RNet 9600 series. Power is preferably provided by a battery pack, preferably rechargeable.

FIG. 7 shows, in addition to the multiplexer 130 which receives the signals from the sensors and distributes them as called for, a signal processing unit 140 and a transmitter and modem unit 150. A suitable transmittter is an RNet 9600 unit manufactured by Motorola Inc. Radius Division, Schaumberg, Ill., which transmits at 464 MHz FM with a frequency deviation of 7.5 KHz. The signal processing unit 140 can include an analog to digital converter (ADC) which digitizes the analog signals from the multiplexer, a timing and control unit 144 which instructs the multiplexer on the distribution of signals from the sensors to the ADC 142. The sensors are in one embodiment sequentially sampled at a 2 Hz rate and digitized to 6 bits, and two address bits are appended to identify from which of the four sensors the data word is generated. The 8-bit words are applied sequentially to UART 152 which converts them to a standard 9600 baud even parity 2-stop bit message.

A microprocessor 146 can be employed to enable storage and manipulation of digitized signals from the sensors. For example, a microprocessor or other controller can receive signals representative of the temperature within the sterilizer, compare this to a signal representative of a designated temperature ($T_0$) for powering up the transmitter, and subject to the results of the comparison, either waiting or powering up the transmitter to send data to the external controller 300. Similarly, the same sequence can be followed to shut down the unit when the temperature drops below $T_0$. As is typical, the microprocessor preferably includes a clock and appropriate software to record the times at which various temperature, pressure an/or moisture measurements are made. Also the unit can be shut down and a warning given when the temperature exceeds a preselected upper value.

The microprocessor can also be provided with means to store the sensor data for transmission to the controller or other signal processor only after removal from the chamber. To facilitate this type of transfer, a hard data link such as by female receptacle 128 on the test device 100 and a male plug 310 on the control unit can be provided to electrically couple the two units. Alternatively, other data transmission means, including those based on infrared transmission, can be employed.

Figure 3:
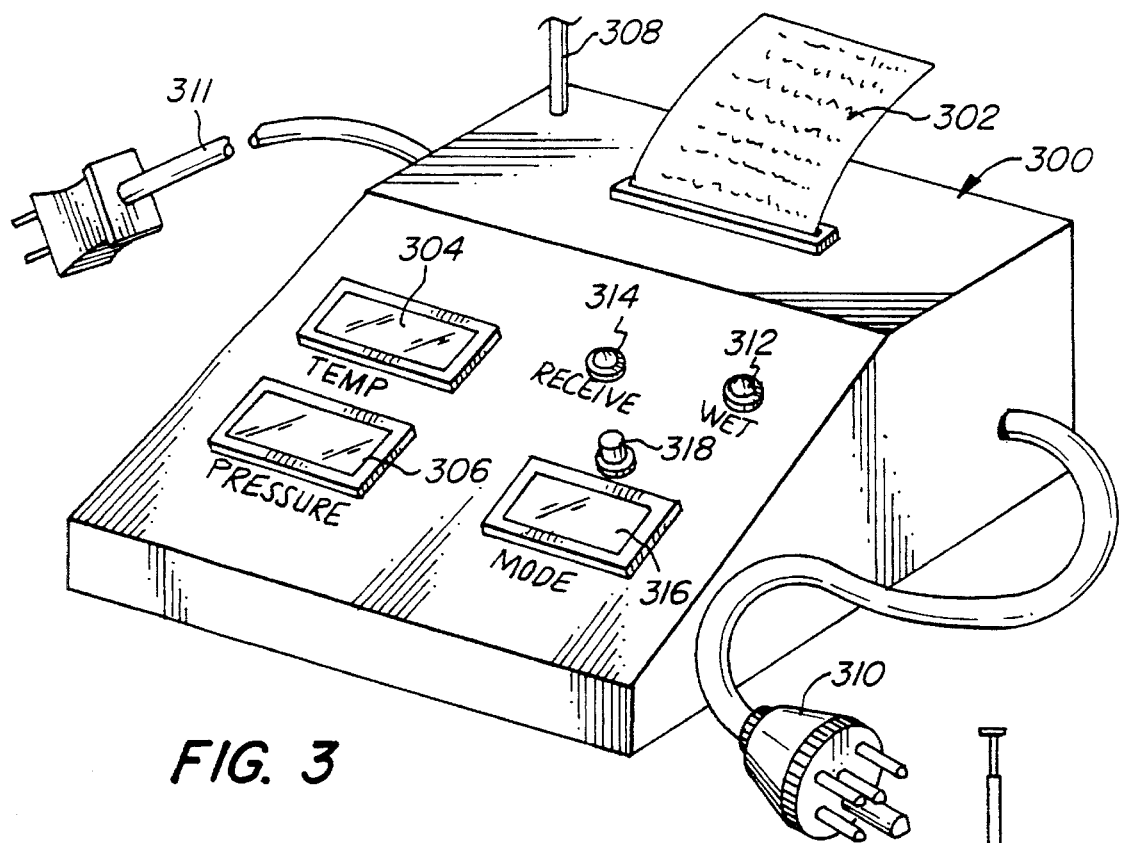
FIG. 3 is a perspective view of a preferred form of controller unit of the invention.
Figure 4:
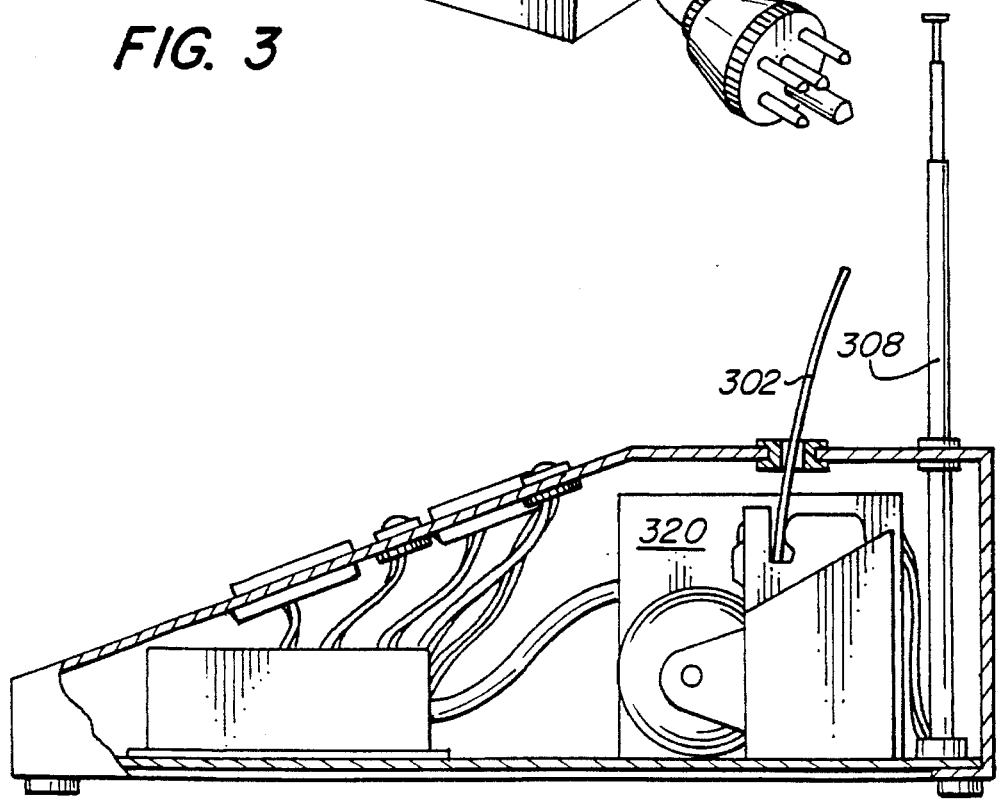
FIG. 4 is a side elevation view of the controller unit shown in FIG. 3, partially cut away to illustrate major components.
Figure 8:
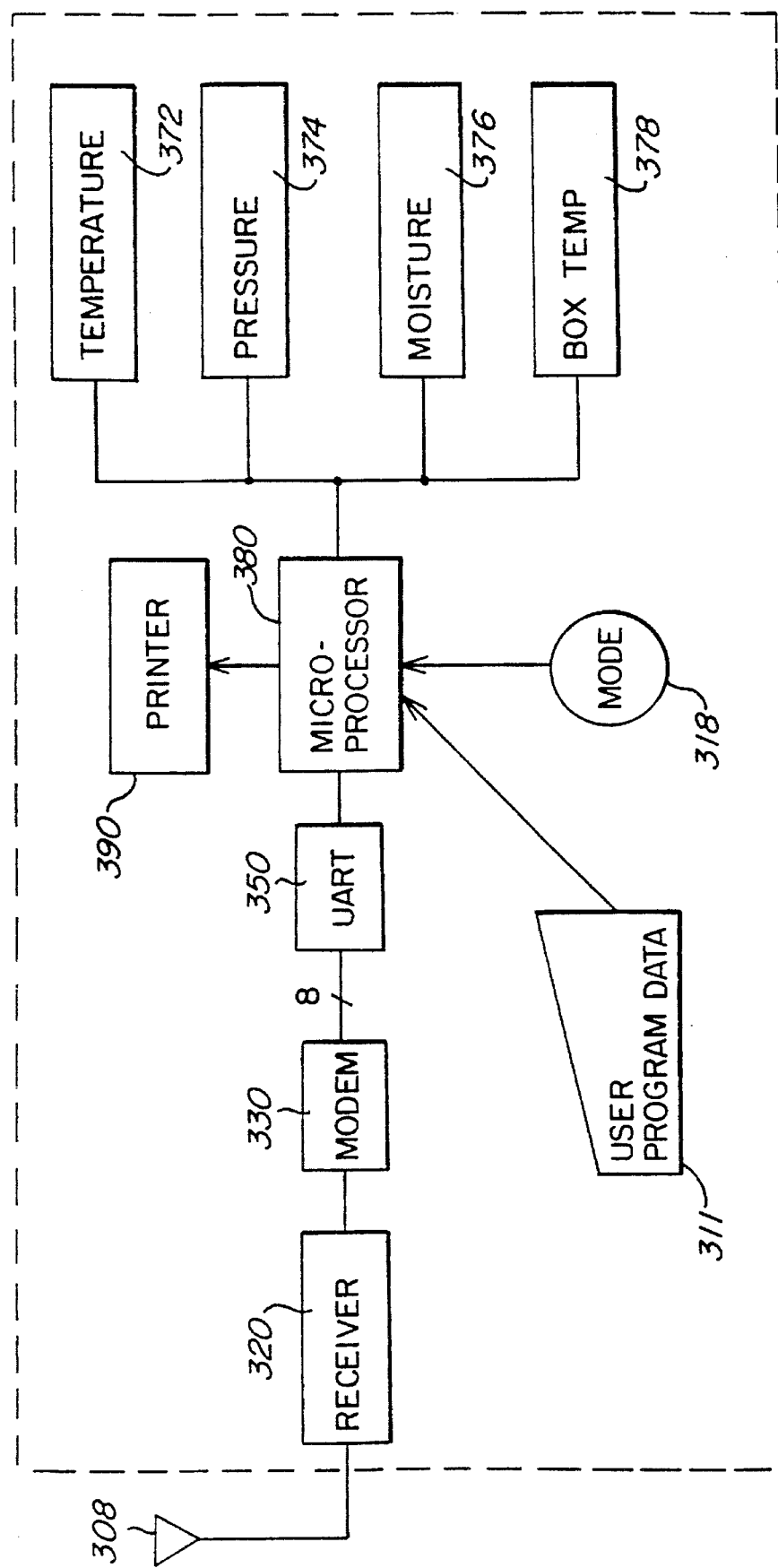
FIG. 8 is a block diagram of the circuitry for a controller unit such as shown in FIG. 3.

FIGS. 3 and 4 show the principal components of a preferred controller 300 according to the invention, and FIG. 8 shows the arrangement of the components in a block diagram. The controller can display the test results in printed form 302 in any desired format and can provide real time indication of conditions on displays (e.g., liquid crystal) for temperature 304 and pressure 306. Data on the conditions inside the steam sterilizer chamber is received preferably by radio, employing antenna 308. Alternatively, as discussed above, the data can be transmitted after the transmitter unit is removed from the sterilizer through a wired data link employing male plug 310. The face of the controller is also shown to include indicators (e.g., light emitting diodes) which provide visual warning of a wet condition 312 in the sterilizer and confirmation of effective reception 314 of transmission from the transmission unit. Power can be provided from standard current through line 311 or from a designated source, as desired.

In its preferred form, the system will be capable of operation in at least of two modes: (1) a Bowie and Dick test mode, typically run once a day (e.g., each morning) on an empty sterilizer, and (2) a test under load. The particular reference temperatures, and if employed, reference pressures and moistures which are referred to determine the effectiveness of operation of the sterilizer, will differ depending on whether or not a load is present. Accordingly, the controller must be set for the particular mode for each cycle of operation and be programmed with the reference conditions for that mode. The load mode reference conditions will typically be unique to an individual sterilizer. The microprocessor is preferably programmed to receive reference temperature, pressure and moisture data by a trained operator, periodically, via data link such as 310. Reference to FIG. 8 shows a user program data block 311 which can be a keyboard, disk drive or other suitable data entry device.

To assure that the proper mode of operation has been selected by the operator, a mode switch 318 includes a light source which will flash until a mode (as displayed on panel 316) is selected by actuating the switch. The controller preferably includes means which prevent the test cycle from beginning and any report to be printed until the mode switch is activated.

Figure 8A:
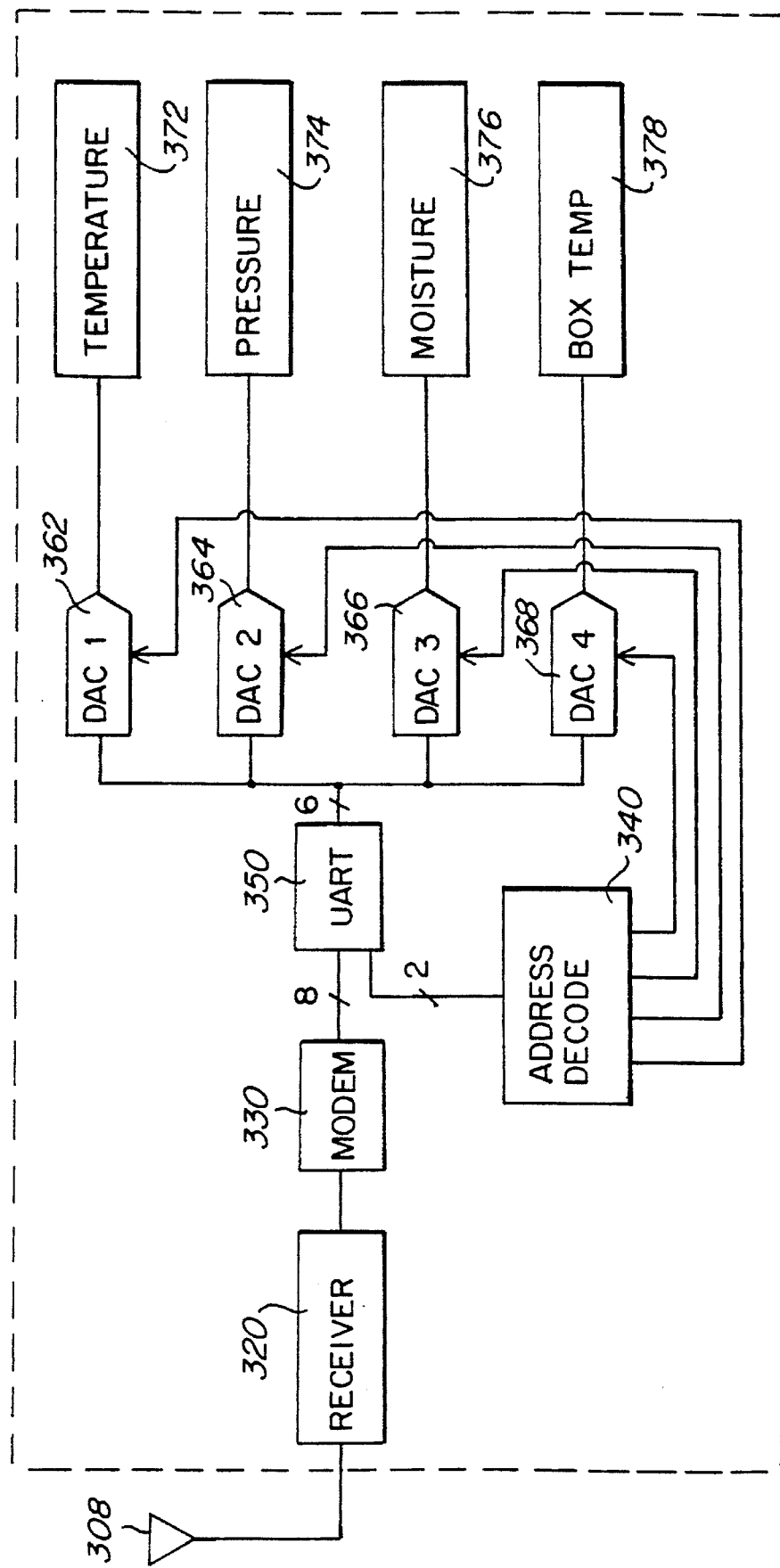
FIG. 8A is a block diagram illustrating a simplified circuitry for a controller unit.

The controller components are illustrated in block form for a preferred device in FIG. 8 and for a simplified version in FIG. 8A. This latter FIGURE shows a radio receiver 320 which receives the data transmission from the transmitter in test unit 100 inside the steam sterilizer 200 and sends the data to UART 330. The UART 350, address decode unit 340 manipulates the data and distributes the designated signals to digital to analog converters (DAC), e.g. strobe driven, (362, 364, 366 and 368) as needed to display the temperature 372, pressure 374, moisture 376 and transmitter temperature 378. Of these, the temperature display 372 is most preferred. The moisture is preferably handled simply by a warning light, and excessive temperatures within the transmitter itself are noted by visual indicator similar to wet indicator 312, which can be accompanied by an audible warning.

Figure 9:
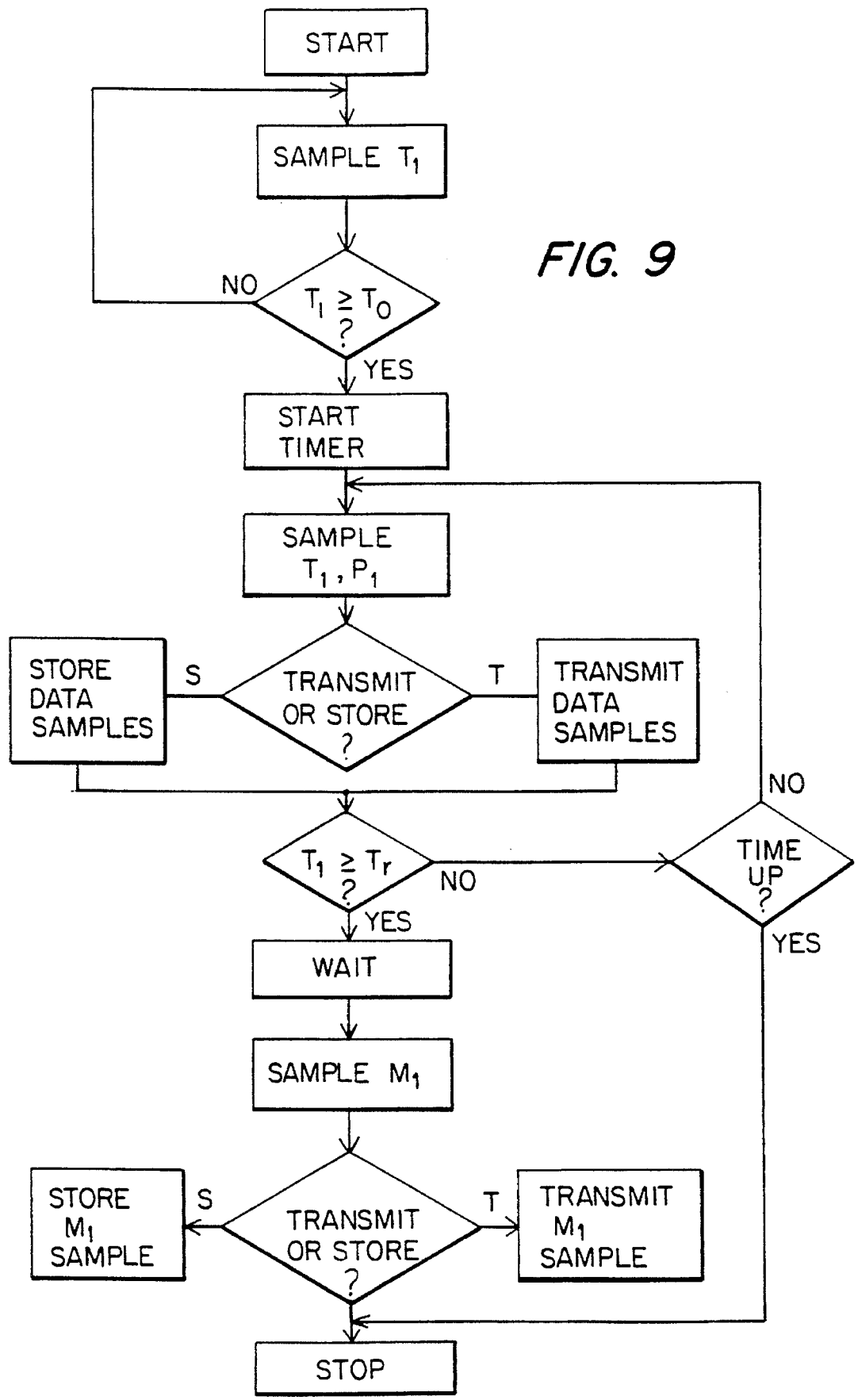
FIG. 9 is a flow-chart depicting the operation of a preferred test unit according to the invention.
Figure 10:
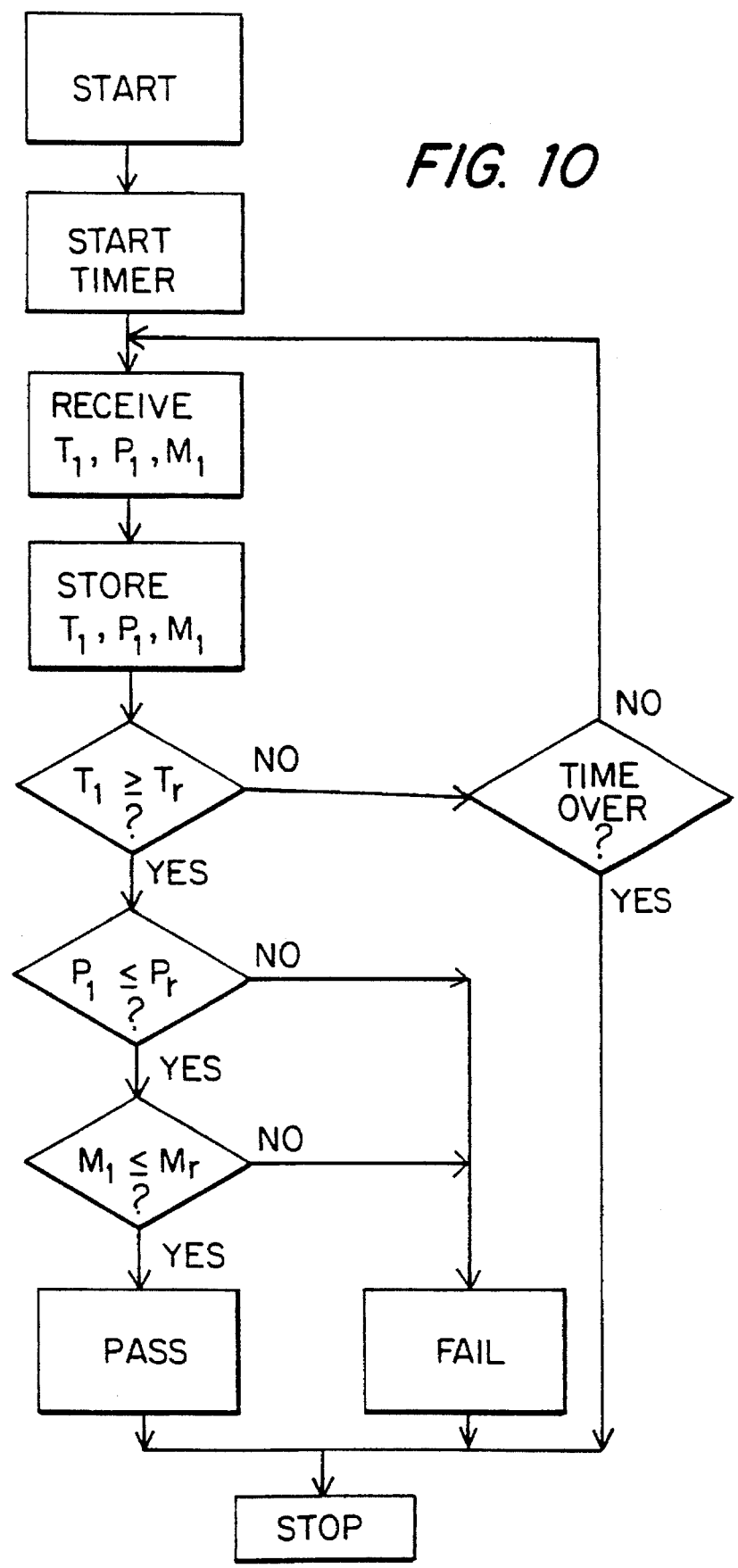
FIG. 10 is a flow chart depicting the operation of a preferred controller unit according to the invention.

The operation of a preferred system can be followed by viewing FIGS. 9 and 10. FIG. 9 is a preferred flow diagram for the operation of a test unit 100, and FIG. 10 is a preferred flow diagram for the operation of a controller 300.

FIG. 8 is a preferred embodiment of a controller in block diagram form showing a receiver 320, a modem 330, a UART 350, and a microprocessor 380 which drives the condition monitors 372, 374, 376 and 378. The microprocessor is instructed as to the mode of operation by mode switch 382, and other data can be input by user program data entry device 311 which can be a keyboard, disc drive, or the like. As is typical, the microprocessor preferably includes a clock and appropriate software to record the times at which various temperature, pressure an/or moisture measurements are made. Output to printer 390 will generate a printed report.

In one preferred Bowie and Dick mode operation, a sterilizer having a preliminary vacuum cycle is opened and the test unit 100 is placed therein. The sterilizer cycle is then begun, and a vacuum is drawn for the designated period of time. This is followed by the introduction of steam at a designated temperature (e.g., 275° F.) for a designated time (e.g., 4.5 minutes). The test unit continuously monitors the temperature (preferably noting the time also). Analog data from this and other transducers is continuously digitized and presented to the microprocessor.

When the temperature reaches a designated $T_0$ value, the test unit is turned on to collect and store test temperature values, $T_1$ and $P_1$ (and preferably the time at which they were taken). Temperature $T_1$ and the signal generated are indicative of the temperature at the location of temperature sensor 122 in cavity 115. Pressure $P_1$ and the signal generated, are indicative of the pressure within cavity 115. Stored within memory is reference temperature information, and a signal $T_r$ is generated indicative of this reference temperature. The reference temperature can be a predetermined temperature, e.g. 275° F., or a calculated value based on a computed average of selected values from earlier runs, e.g., the last ten Bowie and Dick mode temperatures. When the comparison of $T_1$ to $T_r$ indicates that the desired temperature has been reached, sampling for $M_1$ is conducted. The test data is then converted from analog to digital and either stored coded and transmitted.

The controller 300 or functional equivalent preferably receives transmitted test data and processes it in accordance with FIG. 10. The controller receives and stores data indicative of $T_1$, $P_1$ and $M_1$, and then compares signal $T_1$ to a stored signal $T_r$ which is typically the intended sterilization temperature. If this test is met and if pressure data is being treated, signal $P_1$ will be compared to signal $P_r$ indicative of a reference pressure. The reference pressure can be a pressure obtained from stored steam table information to indicate the pressure for saturated steam at that temperature with or without a designated tolerance. For example, the signal $P_r$ can take into account a permissible 5° or 10° F. degrees of superheat. In other words $P_r$ can be slightly higher than the value for saturated steam at $T_1$. After comparison for temperature, and if desired pressure, the logic is queried to assure that the test time, or shorter time for the comparison, has not expired. Moisture data can then be taken and compared to a reference moisture, and a report printed.

In the load mode, various packages undergoing sterilization will be located within the sterilization chamber. Air from each may remain following evacuation. It is not possible to determine effective operation based on Bowie and Dick mode comparisons alone, but reference temperatures, pressures and moistures for this mode can be programmed into the microprocessor for comparisons during the load mode. Moreover, for both modes reference may be had to calculated values based on selected past data. In the Bowie and Dick mode this may be for the last ten final temperatures taken in this mode. In the load mode, a template of time and temperature readings characteristic of effective operation is preferred.

The above description is for the purpose of teaching the person of ordinary skill in the art how to practice the invention, and is not intended to detail all of those obvious modifications and variations of it which will become apparent to the skilled worker upon reading the description. It is intended, however, that all such obvious modifications and variations be included within the scope of the invention which is defined by the following claims. The claims are meant to cover the claimed elements and steps in any arrangement or sequence which is effective to meet the objectives there intended, unless the context specifically indicates the contrary.

I claim:

1. A method for determining the effectiveness of air removal from the chamber of a steam sterilizer, for the detection of air leaks and for monitoring the sterilization conditions within the chamber comprising:

placing within a chamber of a sterilizer a test device having a structure capable of concentrating and trapping small amounts of air critical to the sterilization process to the location of a temperature sensor and sensing a temperature by means of the temperature sensor and generating a signal ($T_1$) indicative of the measured temperature, wherein said test device including wall members defining an elongated cavity with a predetermined length and cross section having an opening at one end of the cavity to permit the entrance of ambient gases, a temperature sensor capable of generating signal $T_1$ indicative of the temperature at its location at the end of the test cavity opposite from said opening and a heat sink capable of condensing steam disposed within the cavity between the opening and the temperature sensor to thereby concentrate any air present in the chamber in the direct vicinity of the temperature sensor, said heat sink comprising a material of a density, porosity and thermal conductivity effective to condense a sufficient amount of steam to cause air, if present, to collect at the end of the test device where the temperature sensor is located;

generating a signal $T_1$;

generating a signal ($T_r$) indicative of a reference temperature;

comparing signal $T_1$ to signal $T_r$; and generating a signal indicative of either a pass or fail condition based on the results of the comparison.

2. A method according to claim 1 wherein the method is set in operation under load mode and the reference temperature is selected to provide appropriate sensitivity for determining the effectiveness of air exclusion from the chamber under operational load conditions.

3. A method according to claim 1 wherein the method is set in the Bowie and Dick mode and the reference temperature is selected to provide appropriate sensitivity for determining the effectiveness of air exclusion from the chamber under no load conditions.

4. A method according to claim 1 which further includes the steps of: storing signal $T_1$ within storage means within said chamber; removing said storage means from said chamber; linking said storage means to a logic circuit outside of said chamber to make said comparison; and displaying the results of said comparison in an archiveable, visual form.

5. A method according to claim 1 which further enables determining the quality of the steam in the chamber and includes the steps of: sensing the pressure within said chamber and generating a signal ($P_1$) indicative thereof; identifying from steam table data the pressure for saturated steam at the temperature corresponding to signal $T_1$ and generating a signal ($P_r$) indicative thereof; comparing signal $P_1$ to signal $P_r$; and generating a signal indicative of either a pass or fail condition based on the results of the comparison.

6. A method according to claim 1 wherein signal $T_1$ and the time at which it was taken are transmitted by radio transmission to a radio receiver located outside of the chamber wherein the antenna of said radio receiver is located outside the chamber and said comparison is displayed in an archivable, visual form.

7. A method according to claim 1 which further enables determining the quality of the steam in the chamber and wet pack conditions, and includes the steps of: by means of a liquid moisture detector in contact with a heat sink that simulates a pack to be sterilized and capable of sensing liquid moisture in the heat sink material, sensing liquid moisture, if present, in the heat sink material and generating a signal ($M_1$) indicative thereof; generating a signal ($M_r$) indicative of a reference value; comparing $M_1$ to signal $M_r$; and generating a signal indicative of either a pass or fail condition based on the results of the comparison 8. A method according to claim 7 which further includes the steps of: sensing the pressure within said chamber and generating a signal ($P_1$) indicative thereof; identifying from steam table data the pressure for saturated steam at the temperature corresponding to signal $T_1$ and generating a signal ($P_r$) indicative thereof; comparing signal $P_1$ to signal $P_r$; and generating a signal indicative of either a pass or fail condition based on the results of the comparison.

9. A method according to claim 1 for assuring effective operation of a sterilizer, further comprising: transmitting signal $T_1$ to a location outside of the sterilization chamber by radio transmission to a receiver that includes an antenna located outside of the chamber and the results of said comparison are displayed in an archivable, visual form; sensing the presence of liquid water dispersed in the steam; and comparing the sensed value of dispersed liquid water to a target level to thereby reduce the chances that wet loads could result due to steam moisture contents higher than the target level.

10. A test device for use in determining the effectiveness of air removal from the chamber of a steam sterilizer, for the detection of air leaks and for monitoring the sterilization conditions within the chamber comprising:

wall member defining an elongated cavity with a predetermined length and cross section having an opening at one end to permit the entrance of ambient gases, a temperature sensor capable of generating signal ($T_1$) indicative of the temperature at its location at the end of the test cavity opposite from said opening; and a heat sink located in said test cavity between said opening and said temperature sensor, said heat sink comprising a material of a density, porosity and thermal conductivity effective to condense a sufficient amount of steam to cause air, if present, to collect at the end of the test device where the temperature sensor is located;

11. A test device according to claim 10 which further includes storage means for storing signal $T_1$ within the chamber of a steam sterilizer.

12. A test device according to claim 10 which further includes means for sensing the pressure within said chamber and generating a signal ($P_1$) indicative thereof.

13. A test device according to claim 10 which further includes means for sensing the moisture within said chamber and generating a signal ($M_1$) indicative thereof.

14. A test device according to claim 10 which further includes a controller comprising:

means for receiving signal ($T_1$);

means for generating a signal ($T_r$) indicative of a reference temperature;

means for comparing signal $T_1$ to signal $T_r$; and means for generating a signal indicative of either a pass or fail condition based on the results of the comparison.

15. A controller according to claim 14 wherein said means for receiving the signal $T_1$ comprises a radio receiver.

16. A system for determining the effectiveness of air removal from a steam sterilizer, for the detection of air leaks and for monitoring the sterilization conditions within the chamber comprising: a test device capable of sensing a temperature at its location and generating a signal ($T_1$) indicative thereof said test device comprising a temperature sensor and means for concentrating and trapping small amounts of air to the location of a temperature sensor, having walled members defining an elongated cavity with a predetermined length and cross section with an opening at one end of the cavity to permit the entrance of steam, a temperature sensor within the cavity displaced from the opening, and a heat sink located in said test module cavity disposed within the cavity between the opening and the temperature sensor, said heat sink, being capable of condensing steam to thereby concentrate any air present in the chamber in the direct vicinity of the temperature sensor, said heat sink comprising a material of a density, porosity and thermal conductivity effective to condense a sufficient amount of steam to cause air, if present, to collect at the end of the test device where the temperature sensor is located;

means for generating a signal ($T_r$) indicative of a reference temperature, which can be either a preselected reference temperature such as the desired sterilization temperature or a calculated temperature such as the average of the last temperature reported in the latest 10 cycles of operation;

means for comparing signal $T_1$ to signal $T_r$; and means for generating a signal indicative of either a pass or fail condition based on the results of the comparison.

17. A system according to claim 16 which further includes:

storage means for storing signal $T_1$ within the chamber of a steam sterilizer;

a logic circuit outside of said chamber;

means for linking said storage means to said logic circuit to make said comparison; and means for displaying the results of said comparison in an archiveable, visual form.

18. A system according to claim 16 which further includes means for sensing the pressure within said chamber and generating a signal ($P_1$) indicative thereof.

19. A system according to claim 16 which further includes means for sensing the liquid moisture within said chamber and generating a signal ($M_1$) indicative thereof.

20. A system according to claim 16 which further includes radio transmission means for transmitting signal $T_1$ to a location outside of the sterilization chamber.

* * * * *